(12) United States Patent
Bailey et al.

(10) Patent No.: US 6,235,753 B1
(45) Date of Patent: May 22, 2001

(54) INHIBITORS OF THE PRODUCTION OF S-CD23 AND THE SECRETION OF TNF

(75) Inventors: Stuart Bailey, Dorking; Andrew Faller, Epping; David Glynn Smith, Saffron Walden; Derek Richard Buckle, Redhill, all of (GB)

(73) Assignee: SmithKline Beecham p.l.c., Brentford Middlesex (GB)

( * ) Notice: Subject to any disclaimer, the term of this patent is extended or adjusted under 35 U.S.C. 154(b) by 0 days.

(21) Appl. No.: 09/180,547
(22) PCT Filed: May 6, 1997
(86) PCT No.: PCT/EP97/02433
 § 371 Date: Jan. 21, 1999
 § 102(e) Date: Jan. 21, 1999
(87) PCT Pub. No.: WO97/43249
 PCT Pub. Date: Nov. 20, 1997

(30) Foreign Application Priority Data

May 10, 1996 (GB) .................................................. 9609794

(51) Int. Cl.$^7$ ..................... C07C 259/04; C07D 215/12; C07D 215/14; C07D 227/62; C07D 333/56

(52) U.S. Cl. .......................... 514/311; 514/367; 514/443; 514/467; 514/469; 514/575; 546/174; 548/180; 549/58; 549/452; 549/467; 562/623

(58) Field of Search ............................. 560/623; 514/311, 514/367, 443, 467, 469, 575; 546/174; 548/180; 549/58, 452, 467; 562/623

(56) References Cited

FOREIGN PATENT DOCUMENTS

| 2 268 934 | 1/1994 | (GB) . |
| WO 96 19956 | 7/1995 | (GB) . |
| WO 96 02240 | 2/1996 | (GB) . |

OTHER PUBLICATIONS

Green and Wuts, Protective Groups in Organic Synthesis 2nd ed., John Wiley & Sons, Inc., NY 1991.*

* cited by examiner

Primary Examiner—Johann Richter
Assistant Examiner—Brian J. Davis
(74) Attorney, Agent, or Firm—Soma G. Simon; William T. King; Charles M. Kinzig

(57) ABSTRACT

Inhibitors of the Production of s-CD23 and the secretion of TNF are provided.

20 Claims, No Drawings

US 6,235,753 B1

INHIBITORS OF THE PRODUCTION OF S-CD23 AND THE SECRETION OF TNF

FIELD OF THE INVENTION

This invention relates to novel inhibitors of the formation of soluble human CD23 and their use in the treatment of conditions associated with excess production of soluble CD23 (s-CD23) such as autoimmune disease and allergy. The compounds of the invention are also inhibitors of the release of tumour necrosis factor (TNF).

CD23 (the low affinity IgE receptor FceRII, Blast 2), is a 45 kDa type II integral protein expressed on the surface of a variety of mature cells, including B and T lymphocytes, macrophages, natural killer cells, Langerhans cells, monocytes and platelets (Delespesse et al, *Adv Immunol*, 49[1991] 149–191). There is also a CD23-like molecule on eosinophils (Grangette et al, *J Immunol*, 143[1989]3580–3588). CD23 has been implicated in the regulation of the immune response (Delespesse et al, *Immunol Rev*, 125[1992]77–97). Human CD23 exists as two differentially regulated isoforms, a and b, which differ only in the amino acids at the intracellular N-terminus (Yokota et al, *Cell*, 55[1988] 611–618). In man the constitutive a isoform is found only on B-lymphocytes, whereas type b, inducible by IL4, is found on all cells capable of expressing CD23.

Intact, cell bound CD23 (i-CD23) is known to undergo cleavage from the cell surface leading to the formation of a number of well-defined soluble fragments (s-CD23), which are produced as a result of a complex sequence of proteolytic events, the mechanism of which is still poorly understood (Bourget et al *J Biol Chem*, 269[1994]6927–6930). Although not yet proven, it is postulated that the major soluble fragments (Mr 37, 33, 29 and 25 kDa) of these proteolytic events, all of which retain the C-terminal lectin domain common to i-CD23, occur sequentially via initial formation of the 37 kDa fragment (Letellier et al, *J Exp Med*, 172[1990]693–700). An alternative intracellular cleavage pathway leads to a stable 16 kDa fragment differing in the C-terminal domain from i-CD23 (Grenier-Brosette et al, *Eur J Immunol*, 22[1992]1573–1577).

Several activities have been ascribed to membrane bound i-CD23 in humans, all of which have been shown to play a role in IgE regulation. Particular cytotoxicity, c) B cell homing to germinal centres of lymph nodes and spleen, and d) downregulation of IgE synthesis (Delespesse et al, *Adv Immunol*, 49,[1991]149–191). The three higher molecular weight soluble CD23 fragments (Mr 37, 33 and 29 kDa) have multifunctional cytokine properties which appear to play a major role in IgE production. Thus, the excessive formation of s-CD23 has been implicated in the overproduction of IgE, the hallmark of allergic diseases such as extrinsic asthma, rhinitis, allergic conjuctivitis, eczema, atopic dermatitis and anaphylaxis (Sutton and Gould, *Nature*, 366,[1993]421–428). Other biological activities attributed to s-CD23 include the stimulation of B cell growth and the induction of the release of mediators from monocytes. Thus, elevated levels of s-CD23 have been observed in the serum of patients having B-chronic lymphocytic leukaemia (Sarfati et al, *Blood*, 7[1988]94–98) and in the synovial fluids of patients with rheumatoid arthritis (Chomarat et al, *Arthritis and Rheumatism*, 36[1993] 234–242). That there is a role for CD23 in inflammation is suggested by a number of sources. First, sCD23 has been reported to bind to extracellular receptors which when activated are involved in cell-mediated events of inflammation. Thus, sCD23 is reported to directly activate monocyte TNF, IL-1, and IL-6 release (Armant et al, vol 180, *J.Exp. Med.*, 1005–1011 (1994)). CD23 has been reported to interact with the B2-integrin adhesion molecules, CD 11b and CD11c on monocyte/macrophage (S. Lecoanet-Henchoz et al, Immunity, vol 3; 119–125 (1995)) which trigger $NO_2^-$, hydrogen peroxide and cytokine (IL-1, IL-6, and TNF) release. Finally, IL4 or IFN induce the expression of CD23 and its release as sCD23 by human monocytes. Ligation of the membrane bound CD23 receptor with IgEtanti-IgE immune complexes or anti CD23 mAb activates cAMP and IL-6 production and thromboxane B2 formation, demonstrating a receptor-mediated role of CD23 in inflammation.

Because of these various properties of CD23, compounds which inhibit the formation of s-CD23 should have twofold actions of a) enhancing negative feedback inhibition of IgE synthesis by maintaining levels of i-CD23 on the surface of B cells, and b) inhibiting the immunostimulatory cytokine activities of higher molecular weight soluble fragments (Mr 37, 33 and 29 kDa) of s-CD23. In addition, inhibition of CD23 cleavage should mitigate sCD23-induced monocyte activation and mediator formation, thereby reducing the inflammatory response.

TNFα is a pro-inflammatory cytokine which is released from stimulated cells by specific cleavage of a 76-amino acid signal sequence in the inactive precursor to generate the mature form. The cleavage of TNFα has been reported to be carried out by a metalloprotease (Gearing, A. J. H. et al, (1994) Nature 370, 555–557; McGeehan, G. M. et al, (1994) Nature 370, 558–561; Mohler, K. M. et al, (1994) Nature 370, 218–220). Compounds reported to inhibit the cleavage of TNFα by the TNF processing enzyme can be broadly described as matrix metalloprotease inhibitors, particularly of the hydroxamic acid class.

TNFα is induced in a variety of cell types in response to bacteria, endotoxin, various viruses and parasites, so that one physiological function ascribed to TNFα is a contribution to the inflammatory response to acute infection by bacteria, parasites, etc (Dinarello, C. A. (1992) Immunol. 4, 133–145). Overproduction of TNFα has been implicated in disease states such as rheumatoid arthritis, septic shock, Crohn's disease and cachexia (Dinarello, 1992). Inhibition of processing of TNFα to the mature, active form would therefore be beneficial in the treatment of these inflammatory disorders. TNFα may also contribute to the destruction of tissue in autoimmune disease although it is not a initiating factor in these diseases. Confirming the importance of TNFα in rheumatoid arthritis, TNFα antibodies have been shown to reduce the severity of disease in short term studies in rheumatoid arthritis models (Elliott, M. J., et al (1993) Arthrit. Rheum. 12, 1681–1690; Elliott et al (1994) Lancet 344, 1125–1127).

International Patent Application No. WO 96/02240 (Smithkline Beecham plc) discloses that compounds which inhibit the action of matrix metalloproteases (eg collagenase, stromelysin and gelatinase) are effective inhibitors of the release of human soluble CD23 transfected into mammalian cell culture systems.

UK Patent Application No. 9601041.8 (Smithkline Beecham plc) discloses that certain compounds of formula (I) are effective inhibitors of the release of human soluble CD23 transfected into mammalian cell culture systems:

SUMMARY OF THE INVENTION

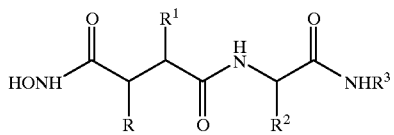

(I)

According to the present invention, there is provided a compound of formula (I) above, wherein:

R is hydroxy, hydrogen, alkyl, alkenyl, alkynyl or aryl;

$R^1$ is arylmethyl or heterocyclylmethyl;

$R^2$ is alkyl, alkenyl, aryl, cycloalkyl or cycloalkenyl; and $R^3$ is hydrogen, alkyl, alkenyl, alkynyl or aryl;

with the proviso that;

if $R^1$ is phenylmethyl or naphthylmethyl, wherein the phenyl or naphthyl group is unsubstituted or substituted by up to five substituents selected from the group consisting of halogen,$(C_{1-6})$alkyl,aryl$(C_{1-6})$alkyl,$(C_{1-6})$ alkoxy, $(C_{1-6})$alkoxy$(C_{1-6})$alkyl, halo$(C_{1-6})$alkyl, hydroxy, nitro, amino, mono- and di-N-$(C_{1-6})$ alkylamino, acylamino, acyloxy, carboxy, carboxy salts, carboxy esters, carbamoyl, mono- and di-N-$(C_{1-6})$alkylcarbamoyl, $(C_{1-6})$alkoxycarbonyl, aryloxycarbonyl, ureido, guanidino, sulphonylamino, aminosulphonyl, $(C_{1-6})$alkylthio, $(C_{1-6})$alkyl sulphinyl $(C_{1-6})$alkylsulphonyl, heterocyclyl, heterocyclyl $(C_{1-6})$ alkyl, and a $(C_{3-5})$alkylene chain linking two adjacent ring carbon atoms to form a carbocyclic ring;

then R is hydroxy.

DETAILED DESCRIPTION OF THE INVENTION

Alkyl, alkenyl and alkynyl groups referred to herein include straight and branched groups containing up to six carbon atoms and are optionally substituted by one or more groups selected from the group consisting of aryl, heterocyclyl, $(C_{1-6})$alkylthio, $(C_{1-6})$alkoxy, aryl$(C_{1-6})$ alkoxy, aryl$(C_{1-6})$alkylthio, amino, mono- or di-$(C_{1-6})$ alkylamino, cycloalkyl, cycloalkenyl, carboxy and esters thereof, hydroxy, and halogen.

Cycloalkyl and cycloalkenyl groups referred to herein include groups having between three and eight ring carbon atoms and are optionally substituted as described hereinabove for alkyl, alkenyl and alkynyl groups.

When used herein, the term "aryl" means single and fused rings suitably containing from 4 to 7, preferably 5 or 6, ring atoms in each ring, which rings, may each be unsubstituted or substituted by, for example, up to three substituents. A fused ring system may include aliphatic rings and need include only one aromatic ring.

Suitable aryl groups include phenyl and naphthyl such as 1-naphthyl or 2-naphthyl.

Suitably any aryl group, including phenyl and naphthyl, may be optionally substituted by up to five, preferably up to three substituents. Suitable substituents include halogen, $(C_{1-6})$alkyl, aryl, aryl$(C_{1-6})$alkyl, $(C_{1-6})$alkoxy, $(C_{1-6})$alkoxy $(C_{1-6})$alkyl, balo$(C_{1-6})$alkyl, aryl$(C_{1-6})$alkoxy, hydroxy, nitro, cyano, azido, amino, mono- and di-N-$(C_{1-6})$ alkylamino, acylamino, arylcarbonylamino, acyloxy, carboxy, carboxy salts, carboxy esters, carbamoyl, mono- and di-N-$(C_{1-6})$alkylcarbamoyl, $(C_{1-6})$alkoxycarbonyl, aryloxycarbonyl, ureido, guanidino, sulphonylamino, aminosulphonyl, $(C_{1-6})$alkylthio, $(C_{1-6})$alkyl sulphinyl, $(C_{1-6})$alkylsulphonyl, heterocyclyl and heterocyclyl $(C_{1-6})$ alkyl. In addition, two adjacent ring carbon atoms may be linked by a $(C_{3-5})$alkylene chain, to form a carbocyclic ring.

When used herein the terms "heterocyclyl" and "heterocyclic" suitably include, unless otherwise defined, aromatic and non-aromatic, single and fused, rings suitably containing up to four heteroatoms in each ring, each of which is selected from oxygen, nitrogen and sulphur, which rings, may be unsubstituted or substituted by, for example, up to three substituents. Each heterocyclic ring suitably has from 4 to 7, preferably 5 or 6, ring atoms. A fused heterocyclic ring system may include carbocyclic rings and need include only one heterocyclic ring.

Preferably a substituent for a heterocyclyl group is selected from halogen, $(C_{1-6})$alkyl, aryl$(C_{1-6})$alkyl, $(C_{1-6})$ alkoxy, $(C_{1-6})$alkoxy$(C_{1-6})$alkyl, halo$(C_{1-6})$alkyl, hydroxy, amino, mono- and di-N-$(C_{1-6})$alkyl-amino, acylamino, carboxy salts, carboxy esters, carbamoyl, mono- and di-N-$(C_{1-6})$alkylcarbonyl, aryloxycarbonyl, $(C_{1-6})$alkoxycarbonyl $(C_{1-6})$alkyl, aryl, oxy groups, ureido, guanidino, sulphonylamino, aminosulphonyl, $(C_{1-6})$alkylthio, $(C_{1-6})$ alkylsulphinyl, $(C_{1-6})$alkylsulphonyl, heterocyclyl and heterocyclyl$(C_{1-6})$alkyl.

In a particular aspect of the invention, R is hydroxy, $R^1$ is 1- or 2-naphthylmethyl; and/or $R^2$ is benzyl or t-butyl; and/or $R^3$ is hydrogen or methyl. In a further aspect of the invention, R is hydroxy, $R^1$ is optionally substituted, for example para-substituted, benzyl; $R^2$ is t-butyl; and $R^3$ is hydrogen or methyl. In a still further aspect of the invention, each of R to $R^3$ is selected from the group consisting of the values ascribed to it in the Examples hereinbelow. Preferably, the compound of formula (I) of the invention is selected from the group consisting of the compounds described in the Examples hereinbelow.

According to a further aspect, the present invention provides the use of a compound of formula (I) for the production of a medicament for the treatment or prophylaxis of disorders such as allergy, inflammatory disorders and autoimmune disease in which the overproduction of s-CD23 is implicated.

In a further aspect the invention provides a method for the treatment or prophylaxis of disorders such as allergy, inflammatory disorders and autoimmune disease in which the overproduction of s-CD23 is implicated, which method comprises the administration of a compound of formula (I), to a human or non-human mammal in need thereof.

The invention also provides a pharmaceutical composition for the treatment or prophylaxis of disorders such as allergy, inflammatory disorders and autoimmune disease in which the overproduction of s-CD23 is implicated which comprises a compound of formula (I) and optionally a pharmaceutically acceptable carrier therefor.

According to a further aspect, the present invention provides the use of a compound of formula (I) for the production of a medicament for the treatment or prophylaxis of conditions mediated by TNF, including, but not limited to, inflammation, fever, cardiovascular effects, haemorthage, coagulation and acute phase response, cachexia and anorexia, acute infections, shock states, graft versus host reactions and autoimmune disease.

In a further aspect the invention provides a method for the treatment or prophylaxis of conditions mediated by TNF, which method comprises the administration of a compound of formula (I), to a human or non-human mammal in need thereof.

The invention also provides a pharmaceutical composition for the treatment or prophylaxis of conditions mediated by TNF, which comprises a compound of formula (I) and optionally a pharmaceutically acceptable carrier therefor.

In a further aspect the invention provides a method for the treatment or prophylaxis of disorders such as allergy, inflammatory disorders and autoimmune disease in which the overproduction of s-CD23 is implicated, which method comprises the administration to a human or non-human mammal in need thereof of a compound which is an inhibitor of the processing of TNF, with the proviso that the compound is not an inhibitor of a matrix metalloprotease.

Particular inflammatory disorders include CNS disorders such as Alzheimers disease, multiple sclerosis, and multi-infarct dementia, as well as the inflammation mediated sequelae of stroke and head trauma.

It is to be understood that the pharmaceutically acceptable salts, solvates and other pharmaceutically acceptable derivatives of the compound of formula (1) are also included in the present invention.

Salts of compounds of formula (I) include for example acid addition salts derived from inorganic or organic acids, such as hydrochlorides, hydrobromides, hydroiodides, p-toluenesulphonates, phosphates, sulphates, acetates, trifluoroacetates, propionates, citrates, maleates, fumarates, malonates, succinates, lactates, oxalates, tartarates and benzoates.

Salts may also be formed with bases. Such salts include salts derived from inorganic or organic bases, for example alkali metal salts such as sodium or potassium salts, and organic amine salts such as morpholine, piperidine, dimethylamine or diethylamine salts.

It has surprisingly been found that the compounds of the present invention are potent and selective inhibitors of CD23 processing and TNF release, whilst exhibiting reduced collagenase inhibitory activity in comparison with the above-mentioned compounds of the prior art.

The compounds of the invention may be prepared by use of any appropriate conventional method, for example by analogy with the methods disclosed in patent publication GB 2 268 934.

Accordingly, a further aspect of the invention provides a process for preparing a compound of formula (I) as defined hereinabove, which process comprises:

(a) deprotecting a compound of formula (II):

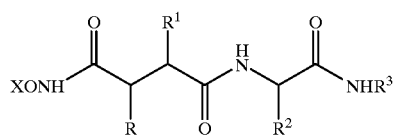

(II)

wherein R to R³ are as defined hereinabove, and X is a protecting group such as benzyl or trimethylsilyl or (b) reacting a compound of formula (III):

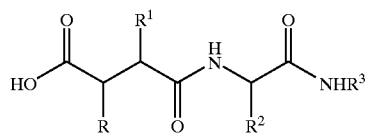

(III)

wherein R to R³ are as defined hereinabove, and any hydroxy group is optionally protected, with hydroxylamine or a salt thereof, or (c) reacting a compound of formula (IV):

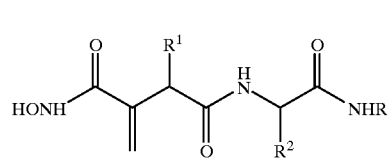

(IV)

wherein R¹ to R³ are as defined hereinabove, with a thiol to give a compound of formula (I) wherein R is methyl substituted by alkylthio, arylthio, aralkylthio, or heterocyclylthio, or (d) converting a compound of formula (a) to a different compound of formula (I) as defined hereinabove.

Compounds of formulae (II) and (III), wherein R is hydroxy or protected hydroxy, and compounds of formula (IV), wherein R¹ is heterocyclylmethyl, are novel and form a further aspect of the invention.

METHODS OF PREPARATION

Compounds of formula (II) can be prepared from compounds of formula (III) by reaction with a protected hydroxylamine. Compounds of formula (III) having one or more protected hydroxy groups can be converted by hydrolysis to a corresponding unprotected compound of formula (III).

Suitable protecting groups for a hydroxamic acid are well known in the art and include benzyl, trimethylsilyl, t-butyl and t-butyldimethylsilyl.

Suitable protecting groups for a carboxylic acid are well known in the art and include t-butyl, benzyl and methyl.

Certain compounds of formula (III) can be prepared by reduction of a compound of formula (V):

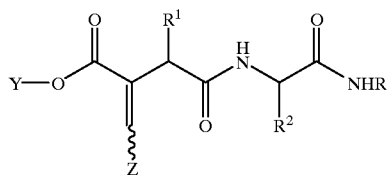

(V)

wherein R¹ to R³ are as defined hereinabove, Y is a protecting group such as t-butyl, and Z is a group such that ZCH₂— is R.

Compounds of formula (III) can also be prepared by reacting a compound of formula (VI):

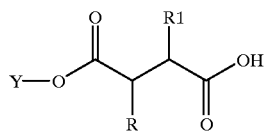
(VI)

wherein R, $R^1$ and Y are as defined hereinabove, with a compound of formula (VII):

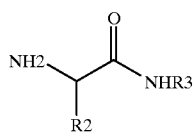
(VII)

wherein $R^2$ and $R^3$ are as defineed hereinabove, or an activated derivative thereof.

Compounds of formula (RII) can also be prepared by reacting a compound of formula (VIII):

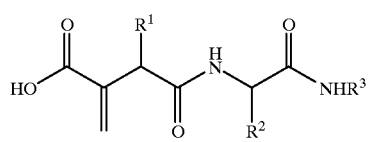
(VIII)

wherein $R^1$ to $R^3$ are as hereinabove defined, with a thiol to give a compound of formula (III) wherein R is methyl substituted by alkylthio, arylthio, aralky-tlio, or heterocyclylthio.

Compounds of formula (VIII) can be prepared by reacting a compound of formula (IX):

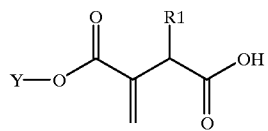
(IX)

wherein $R^1$ and Y are as defined hereinabove, with a compound of formula (VII) as defined hereinabove, or an activated derivative thereof, followed by hydrolysis to remove the protecting group Y.

A specific aspect of the invention provides a process for preparing a compound of formula (I) as defined hereinabove wherein R is hydroxy, which process comprises reacting a compound of formula (X):

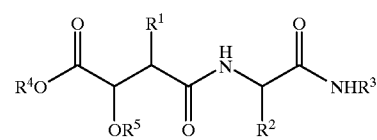
(X)

wherein $R^1$ to $R^3$ are as defined hereinabove, and $R^4$ and $R^5$ are the same or different and each is hydrogen or a hydroxy protecting group, or $R^4$ and $R^5$ together form a divalent hydroxy protecting group, with hydroxylamine or a salt thereof.

Compounds of formula (X) wherein $R^4$ and $R^5$ are hydrogen can be prepared by deprotection (eg hydrolysis and/or deetherification) of a corresponding compound wherein $R^4$ and $R^5$ are not hydrogen.

Compounds of formula (X) wherein $R^4$ and $R^5$ are not hydrogen can be prepared by reacting a compound of formula (XI):

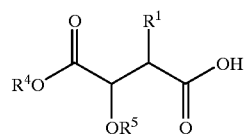
(XI)

wherein $R^1$ $R^4$ and $R^5$ are as defined hereinabove, with a compound of formula (VII) as defined hereinabove.

Preferred compounds of formula (IX) can be prepared by reacting a compound of formula (XII):

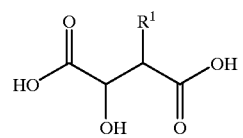
(XII)

wherein $R^1$ is as defined hereinabove, with dimethoxypropane.

Compounds of formula (XII) can be prepared by reacting a diester (such as the dimethyl or diethyl ester) of 2-hydroxy succinic acid with a compound of formula $R^1X'$ in the presence of a strong base such as lithium diisopropylamide, wherein X' is a leaving group such as bromine or iodine, and then hydrolysing the resulting compound to remove the ester groups.

The isomers, including stereoisomers, of the compounds of the present invention may be prepared as mixtures of such isomers or as individual isomers. The individual isomers may be prepared by any appropriate method, for example individual stereoisomers may be prepared by stereospecific chemical synthesis starting from chiral substrates or by separating mixtures of diastereoisomers using known methods. In a preferred aspect, the invention provides compounds of formula (IA):

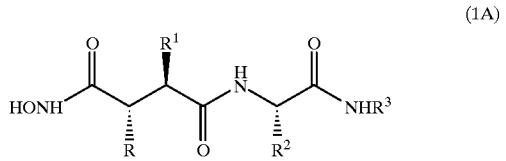
(1A)

It is preferred that the compounds are isolated in substantially pure form.

As stated herein an inhibitor of the formation of soluble human CD23 has useful medical properties. Preferably the active compounds are administered as pharmaceutically acceptable compositions.

The compositions are preferably adapted for oral administration. However, they may be adapted for other modes of administration, for example in the form of a spray, aerosol or other conventional method for inhalation, for treating respiratory tract disorders; or parenteral administration for patients suffering from heart failure. Other alternative modes of administration include sublingual or transdermal administration.

The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling or tabletting. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Compositions of this invention may also suitably be presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns for example diameters in the range of 1–50 microns, 1–10 microns or 1–5 microns. Where appropriate, small amounts of other anti-asthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

The compositions may contain from 0.1% to 99% by weight, preferably from 10–60% by weight, of the active material, depending upon the method of administration. A preferred range for inhaled administration is 10–99%, especially 60–99%, for example 90, 95 or 99%.

Microfine powder formulations may suitably be administered in an aerosol as a metered dose or by means of a suitable breath-activated device.

Suitable metered dose aerosol formulations comprise conventional propellants, cosolvents, such as ethanol, surfactants such as oleyl alcohol, lubricants such as oleyl alcohol, desiccants such as calcium sulphate and density modifiers such as sodium chloride.

Suitable solutions for a nebulizer are isotonic sterilised solutions, optionally buffered, at for example between pH 4–7, containing up to 20 mg/ml of compound but more generally 0.1 to 10 mg/ml, for use with standard nebulisation equipment.

An effective amount will depend on the relative efficacy of the compounds of the present invention, the severity of the disorder being treated and the weight of the sufferer. Suitably, a unit dose form of a composition of the invention may contain from 0.1 to 1000 mg of a compound of the invention (0.001 to 10 mg via inhalation) and more usually from 1 to 500 mg, for example 1 to 25 or 5 to 500 mg. Such compositions may be administered from 1 to 6 times a day, more usually from 2 to 4 times a day, in a manner such that the daily dose is from 1mg to 1 g for a 70 kg human adult and more particularly from 5 to 500 mg. That is in the range of about $1.4 \times 10^{-2}$ mg/kg/day to 14 mg/kg/day and more particularly in the range of about $7 \times 10^{-2}$ mg/kg/day to 7 mg/kg/day.

The following examples illustrate the invention but do not limit it in any way.

BIOLOGICAL TEST METHODS

Procedure 1: The ability of test compounds to inhibit the release of soluble CD23 was investigated by use of the following procedure.

RPMI 8866 Cell membrane CD23 cleavage activity assay:

Plasma membranes from RPMI 8866 cells, a human Epstein-Barr virus transformed B-cell line (Sarfati et al., Immunology 60 [1987]539–547) expressing high levels of CD23 are purified using an aqueous extraction method. Cells resuspended in homogenization buffer (20 mM HEPES pH 7.4, 150 mM NaCl, 1.5 mM MgCl2, 1 mM DTI) are broken by $N_2$ cavitation in a Parr bomb and the plasma membrane fraction mixed with other membranes is recovered by centrifugation at 10,000×g. The light pellet is resuspended in 0.2 M potassium phosphate, pH 7.2 using 2 ml per 1–3 g wet cells and the nuclear pellet is discarded. The membranes are further fractionated by partitioning between at 0.25 M sucrose in a total of 16 g per 10–15 mg membrane proteins [Morre and Morre, BioTechniques 7, 946–957 (1989)]. The phases are separated by brief centrifugation at 1000×g and the PEG (upper) phase is collected, diluted 3–5 fold with 20 mM potassium phosphate buffer pH 7.4, and centrifuged at 100,000×g to recover membranes in that phase. The pellet is resuspended in phosphate-buffered saline and consists of 3–4 fold enriched plasma membranes as well as some other cell membranes (e.g. lysosomes, Golgi). The membranes are aliquoted and stored at −80° C. Fractionation at 6.6% Dextran/PEG yields plasma membranes enriched 10-fold.

The fractionated membranes are incubated at 37° C. for times up to 4 hrs to produce fragments of CD23 which are separated from the membrane by filtration in 0.2 micron Durapore filter plates (Millipore) after quenching the assay with 5 uM Preparation 1 from P 30994. sCD23 released from the membrane is determined using the EIA kit from The Binding Site (Birmingham, UK) or a similar one utilizing MHM6 anti-CD23 mAb [Rowe et al., Int. J. Cancer, 29, 373–382 (1982)] or another anti-CD23 mAb as the capture antibody in a sandwich EIA. The amount of soluble CD23 made by 0.5 ug membrane protein in a total volume of 50 ul phosphate-buffered saline is measured by EIA and compared to the amount made in the presence of various concentrations of inhibitors. Inhibitors are prepared in solutions of water or dimethylsulfoxide (DMSO) and the final DMSO concentration is not more than 2%. IC50's are determined by curve fitting as the concentration where 50% inhibition of production of sCD23 is observed relative to the difference in sCD23 between controls incubated without inhibitor.
Procedure 2: The ability of test compounds to inhibit collagenase was investigated using the following procedure.
Collagenase Inhibition Assay:

The potency of compounds to act as inhibitors of collagenase was determined by the method of Cawston and Barrett (Anal. Biochem. 99, 340–345, 1979), hereby incorporated by reference, whereby a 1 mM solution of the inhibitor being tested or dilutions thereof, was incubated at 37° C. for 18 h with collagen and human recombinant collagenase, from synovial fibroblasts cloned, expressed and purified from *E. Coli*, (buffered with 150 mM Tris, pH 7.6, containing 15 mM calcium chloride, 0.05% Brij 35, 200 mM sodium chloride and 0.02% sodium azide). The collagen was acetylated $^3$H type 1 bovine collagen prepared by the method of Cawston and Murphy (methods in Enzymology 80, 711,1981) The samples were centrifuged to sediment undigested collagen and an aliquot of the radioactive supernatant removed for assay on a scintillation counter as a measure of hydrolysis. The collagenase activity in the presence of 1 mM inhibitor, or dilution thereof, was compared to activity in a control devoid of inhibitor and the results reported as that concentration effecting 50% of the collagenase ($IC_{50}$).
Procedure 3: The ability of test compounds to inhibit TNF release was investigated using the following procedure.

Assay for inhibition of release of TNFα from human monocytes stimulated by lipopolysaccharide (LPS) endotoxin.

Human monocytes, cultured in RPMI 1640 medium supplemented with 10% fetal calf serum, are centrifuged at 1000×g for 5 min and then resuspended in medium at 2×10$^6$ cells/ml. The cell suspension is aliquoted in 24 well plates, 1 ml per well. Compounds to be tested are dissolved in neat dimethyl sulfoxide (DMSO) and added to culture with the final DMSO concentration at 0.1%. Compounds are added to cells in triplicate wells. TNFα release is stimulated by addition of LPS to the cells at a final concentration of 200 ng/ml. Appropriate control cultures are set up in triplicates also. The plates are incubated for 18–20 hrs at 37° C., 5% $CO_2$, then centrifuged at 1000×g for 5 min. A specific ELISA for human TNFα (SmithKline Beecham) is used to measure TNF levels in the cell-free culture supernatants.

EXAMPLES

Example 1

Preparation of N'-[3S-Hydroxy-4-(N-hydroxyamino)-2R-(2-naphthylmethyl)succinyl]-S-tert-leucine-N-methylamide.

a) Dimethyl 2S-hydroxy-3R-(2-naphthylmethyl) succinate

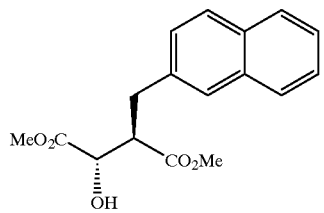

To a solution of diisopropylamine (3.1 ml, 22 mmol) in tetrahydrofuran (30 ml) at −10° C. was added dropwise n-butyllithium (1.6M in hexane, 13.75 ml, 22 mmol). The solution was stirred for 30 min then cooled to −70° C. and a solution of (S)-dimethyl malate (1.6 g, 10 mmol) in tetrahydrofuran (20 ml) added dropwise. After 90 min 2-naphthylmethyl bromide (4.42 g, 22 mmol) was added. The reaction was stirred for 2 h then poured into 2N hydrochloric acid and the product extracted with diethyl ether (3×50 ml). The combined extracts were washed with water (30, ml), sodium bicarbonate (30 ml), brine and dried ($MgSO_4$). Filtration and evaporation gave an oil which was chromatographed on silica. Gradient elution (0–50% ether/hexane) gave (1.08 g) as a white solid mp 91–92° C.
$^1$H NMR ($CDCl_3$) 3.13–3.47 (3H, m), 3.26 (1H, d, J=7 Hz), 3.69 (3H, s), 3.74 (3H, s), 4.12 (1H, dd, J=7, 2.5 Hz), 7.38–7.50 (3H, m), 7.73 (1H, s), 7.81 (4H, br d, J=8 Hz).

b) N'-[2R-(2,2-Dimethyl-4-oxo-1,3-dioxalan-5S-yl)-3-(2-naphthyl)propanoyl]-S-tert-leucine-N-methylamide

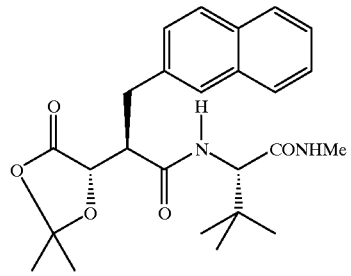

To a solution of dimethyl 2S-hydroxy-3R-(2-naphthylmethyl)succinate (2.0 g, 6.6 mmol) in dioxane (15 ml) and water (30 ml) was added potassium hydroxide (1.11 g). The yellow solution was heated under reflux for 3 h, acidified using Dowex 50×8 resin and concentrated. The resulting pink solid was dissolved in dimethyl formamide (50 ml) and 2,2-dimethoxypropane (50 ml) and tosyl chloride (0.1 g) added. After stirring for 18 h the solution was concentrated. The residue was dissolved in ethyl acetate and washed with sodium bicarbonate solution, dried ($MgSO_4$) and concentrated to a yellow foam (1.664 g). This was dissolved in dry dimethyl formamide (10 ml) and 1-hydroxybenzotriazole hydrate (367 mg), tert leucine methylamide (218 mg, 1.5 mmol) and 1-(3-dimethylaminopropyl)-3-ethylcarbodiimide hydrochloride (312 mg, 1.6 mmol) were added. The solution was stirred for 18 h then concentrated. The residue was dissolved in ethyl acetate and washed with citric acid (10%, 2×20 ml), water (20 ml), sodium bicarbonate solution (20 ml) and brine (10 ml) and dried (MgSO$_4$). Removal of the solvent and chromatograpy of the residue on silica (diethyl ether) gave N'-[2R-(2,2-dimethyl-4-oxo-1,3-dioxalan-5S-yl)-3-(2-naphthyl)propanoyl]-S-tert-leucine-N-methylamide (434 mg) as a white powder mp 118–9° C.

$^1$H NMR (d$_6$ DMSO) 0.84 (9H, s), 1.49 (3H, s), 1.59 (3H, s), 2.33 (3H, d, J=4.5 Hz), 3.0–3.24 (2H, m), 4.16 (1H, d, J=10 Hz), 4.55 (1H, d, J=8.5 Hz), 7.33 (1H, d, J=7 Hz), 7.4–7.5 (2H, m), 7.65 (1H, s), 7.67–7.86 (5H, m).

c) N'-[3S-Hydroxy-4-(N-hydroxyamino)-2R-(2-naphthylmethyl)succinyl]-S-tert-leucine-N-methylamide.

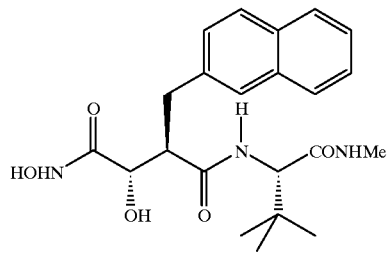

A solution of N'-[2R-(2,2-dimethyl-4-oxo-1,3-dioxalan-5S-yl)-3-(2-naphthyl)propanoyl]-S-tert-leucine-N-methylamide (410 mg, 0.9 mmol), hydroxylamine hydrochloride (259 mg, 3.7 mmol) and N-methylmorpholine (0.41 ml, 3.7 mmol) in methanol (5 ml) was stirred for 24 h. The solution was concentrated, triturated with diethyl ether, water and then filtered to give N'-[3S-hydroxy-4-(N-hydroxyamino)-2R-(2-naphthylmethyl)succinyl]-S-tert-leucine-N-methylamide as a white solid (257 mg) mp 189–90° C.

$^1$H NMR (d$_6$ DMSO) 0.85 (9H, s), 2.25 (3H, d, J=4.5 Hz), 2.74 (1H, dd, J=13.4, 5 Hz), 2.94 (1H, app t, J=11 Hz), 3.07–3.09 (1H, m), 3.86 (1H, t, J=7.5 Hz), 4.09 (1H, d, J=10 Hz), 5.55 (1H, d, J=8 Hz), 7.29 (1H, d, J=8 Hz), 7.4–7.75 (3H, m), 7.51 (1H, s), 7.75–7.85 (4H, m), 8.89 (1H, s) 10.67 (1H, s).

The following compounds were prepared using the method described in Example 1:

Example 2

N'-[3S-Hydroxy-4-(N-hydroxyamino)-2R-(2-naphthylmethyl)succinyl]-S-phenylalanine-N-methylamide

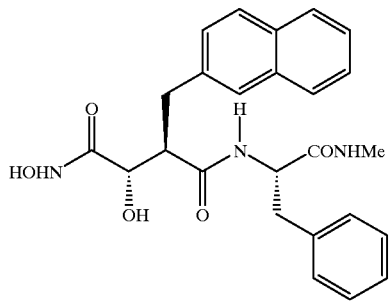

mp 168–70° C. $^1$H NMR (d$_6$ DMSO) 2.28 (3H, d, J=4 Hz), 2.77–2.96 (5H, m), 3.94 (1H, t, J=4 Hz), 4.27 (1H, q, J=5 Hz), 5.77 (1H, d, J=6 Hz), 7.1–7.87 (13H, m), 7.98 (1H, d, J=7,5 Hz), 8.93 (1H, s) 10.74 (1H, s).

Example 3

N'-[3S-Hydroxy-4-(N-hydroxyamino)-2R-(2-naphthylmethyl)succinyl]-S-phenylalaninamide

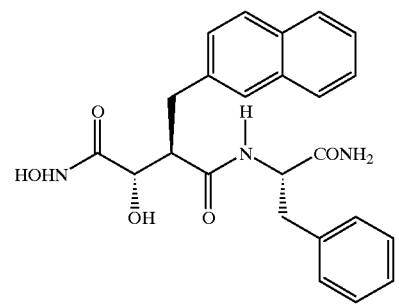

mp 175–7° C. $^1$H NMR (d$_6$ DMSO) 2.75–3.0 (4H, m), 3.01 (1H, dd, J=13.5, 5 Hz), 3.93 (1H, t, J=6 Hz), 4.26 (1H, dd, J=8, 5.5 Hz), 5.82 (1H, d, J=6 Hz), 7.02 (1H, br s), 7.16 (5H, s), 7.22 (2H, d, J=10 Hz), 7.41–7.50 (2H, m), 7.55 (1H, br s), 7.75–7.86 (3H, m), 7.95 (1H, d, J=8 Hz), 8.91 (1H, s) 10.70 (1H, s).

Example 4
N'-[3S-Hydroxy-4-(N-hydroxyamino)-2R-(3-iodobenzyl)succinyl]-S-phenylalaninamide MH$^+$512

Example 5
N'-[3S-Hydroxy-4-(N-hydroxyamino)-2R-(4-methylbenzyl)succinyl]-S-phenylalaninamide MNa$^+$422

Example 6
N'-[3S-Hydroxy-4-(N-hydroxyamino)-2R-(3-methylbenzyl)succinyl]-S-phenylalaninamide MNa$^+$422

Example 7
N'-[3S-Hydroxy-4-(N-hydroxyamino)-2R-(benzyl)succinyl]-S-phenylalaninamide MNa$^+$408

Example 8
N-[3S-Hydroxy-4-(N-hydroxyamino)-2R-(2-methylbenzyl)succinyl]-S-phenylalanine N-methylamide MH$^+$414

Example 9
N'-[3S-Hydroxy-4-(N-hydroxyamino)-2R-(benzyl)succinyl]-S-phenylalanine N-methylamide MH$^+$400

Example 10
N'-[3S-Hydroxy-4-(N-hydroxyamino)-2R-(2-phenylbenzyl)succinyl]-S-phenylalanine N-methylamide MNa$^+$498

Example 11
N'-[3S-Hydroxy-4-(N-hydroxyamino)-2R-(3-iodobenzyl)succinyl]-S-tert-leucine N-methylamide MH$^+$492

Example 12
N'-[3S-Hydroxy-4-(N-hydroxyamino)-2R-(4-methylbenzyl)succinyl]-S-tert-leucine N-methylamide MH$^+$380

Example 13
N'-[3S-Hydroxy-4-(N-hydroxyamino)-2R-(3-methylbenzyl)succinyl]-S-tert-leucine N-methylamide MH$^+$380

Example 14
N'-[3S-Hydroxy-4-(N-hydroxyamino)-2R-(benzyl)succinyl]-S-tert-leucine N-methylamide MH$^+$366

Example 15
N'-[3S-Hydroxy-4-(N-hydroxyamino)-2R-(4-azidobenzyl)succinyl]-S-tert-leucine-N-methylamide MH$^+$407

Example 16

N'-[3S-Hydroxy-4-(N-Hydroxyamino)-2-R-(2-Benzothiophenylmethyl)succinyl]-S-phenylalanamide

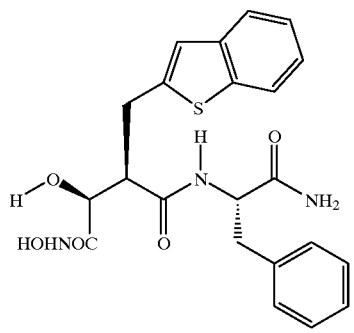

m.p. 189–190° C. 1H NMR, (d⁶ DMSO) 2.8–3.14 (5H, m), 4.00 (1H, t, J=6.5 Hz), 4.31 (1H, dd, J=5,3 Hz), 5.85 (1H, d, J=6.5 Hz), 6.97 (1H, s), 7.06 (1H, br s), 7.15 (5H, S), 7.24–7.32 (2H, m), 7.34 (1H, br s), 7.67 (1H, d, J=7 Hz), 7.84 (1H, d, J=7 Hz), 7.99 (1H, d, J=8 Hz), 8.93 (1H, d, J=2 Hz), 10.70 (1H, d, J=2 Hz).

Example 17

N'-[3S-Hydroxy-4-(N-Hydroxyamino)-2-R-(3-Benzothiophenylmethyl)succinyl]-S-phenylalanine-N-methylamide

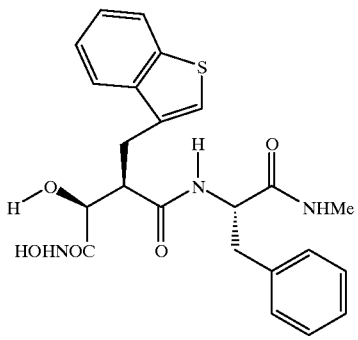

m.p. 148–150° C. MH⁺=456; MNa⁺=478.

Example 18

N'-[3S-Hydroxy-4-(N-Hydroxyamino)-2-R-(2-Benzofuranylmethyl)succinyl]-S-phenylalanine-N-methylamide

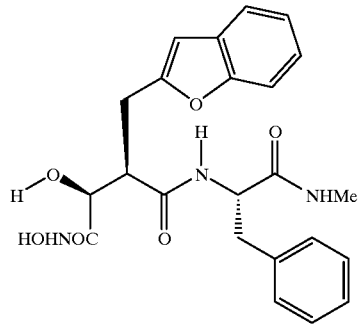

m.p. 160–161° C. 1H NMR, (d⁶ DMSO) 2.43 (3H, d, J=4 Hz), 2.75–3.10 (5H, m), 4.01 (1H, t, J=6 Hz), 4.33 (1H, app q, J=5.5 Hz), 5.86 (1H, d, J=6 Hz), 6.40 (1H, s), 7.02–7.25 (7H, m), 7.44–7.50 (2H, m), 7.66 (1H, q, J=4 Hz), 8.07 (1H, d, J=6 Hz), 8.94 (1H, s), 10.75 (1H, s).

Example 19

N'-[3S-Hydroxy-4-(N-Hydroxyamino)-2-R-(4-Hydroxybenzyl)succinyl]-S-phenylalanamide

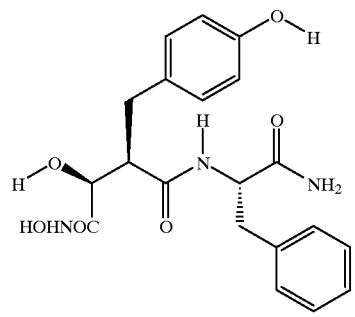

m.p. 154–155° C. 1H NMR, (d⁶ DMSO) 2.49–2.58 (2H, obs), 2.66 (1H, dd, J=14,8 Hz), 2.84 (1H, dd, J=14,8 Hz), 3.08 (1H, dd, J=14,5 Hz), 3.85 (1H, t, J=6.5 Hz), 4.27 (1H, m), 5.74 (1H, d, J=6.5 Hz), 6.58 (2H, d, J=8 Hz), 6.81 (2H, d, J=8 Hz), 7.05 (1H, br s), 7.15–7.26 (6H, m), 7.83 (1H, d, J=8 Hz), 8.86 (1H, s), 9.14 (1H, s), 10.64 (1H, s).

Example 20

N'-[3S-Hydroxy-4-(N-Hydroxyamino)-2-R-(7-Methoxybenzofuranylmethyl)succinyl]-S-phenylalanine-N-methylamide

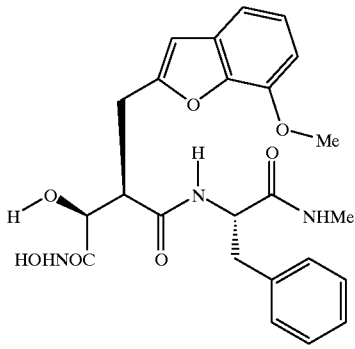

m.p. 161–163° C. MH$^+$=470; MNa$^+$=492.

Example 21

N'-[3S-Hydroxy-4-(N-Hydroxyamino)-2-R-(2-(3-Methyl)benzothiophenylmethyl)succinyl]-S-phenylalanine-N-methylamide

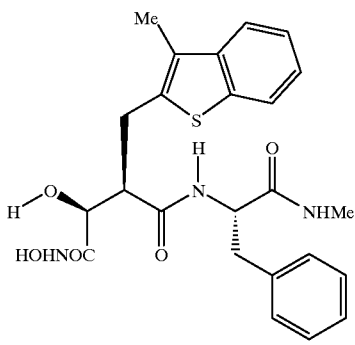

MH$^+$=470; MNa$^+$=492.

Example 22

N'-[3S-Hydroxy-4-(N-Hydroxyamino)-2-R-(4-Benzyloxybenzyl)succinyl]-S-phenylalanamide

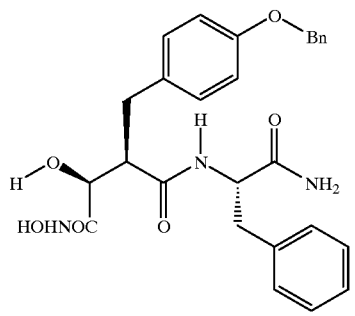

m.p. 179–180° C. (methanol/ethyl acetate). 1H NMR, (d$^6$ DMSO) 2.5–2.93 (4H, m), 3.02 (1H, dd, J=14,5 Hz), 3.86 (1H, t, J=6 Hz), 4.28 (1H, dd, J=14,5 Hz), 5.03 (2H, s), 5.72 (1H, d, J=6 Hz), 6.83 (2H, d, J=8.5 Hz), 6.93 (2H, d, J=8.5 Hz), 7.04 (1H, s), 7.08 (1H, s), 7.1–7.3 (5H, m), 7.3–7.5 (5H, m), 7.86 (1H, d, J=5 8 Hz), 8.86 (1H, s), 10.64 (1H, s).

Example 23

N'-[3S-Hydroxy-4-(N-Hydroxyamino)-2-R-(3,4-Dimethylbenzyl)succinyl]-S-phenylalanine-N-methylamide

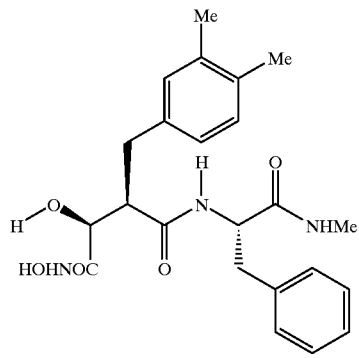

m.p. 163–165° C. MH$^+$=428.

Example 24

N'-[3S-Hydroxy-4-(N-Hydroxyamino)-2-R-(4-(prop-2-yl)benzyl)succinyl]-S-phenylalanamide

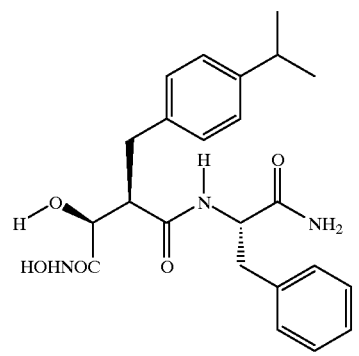

m.p. 168–170° C. MNa$^+$=450.

Example 25

N'-[3S-Hydroxy-4-(N-hydroxyamino)-2R-(2-benzthiazalylmethyl)succinyl]-S-tert-leucine N-methylamide

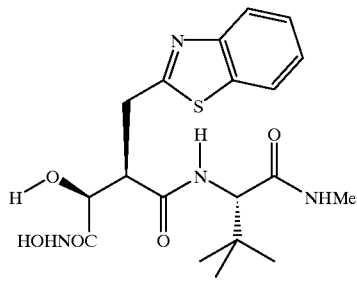

m.p. 132–134° C. 1H NMR, (d$^6$ DMSO) 0.86 (9H, s), 2.39 (3H, d, J=4.5 Hz), 2.5–2.6 (1H, obs), 3.0–3.24 (2H, m), 3.95 (1H, t, J=3 Hz), 4.15 (1H, d, J=8 Hz), 7.4–7.7 (33H, m), 7.75 (1H, br q, J=4.5 Hz), 7.88 (1H, d, J=9 Hz), 8.9 (1H, s), 10.73 (1H, s).

Example 26

N'-[3S-Hydroxy-4-(N-Hydroxyamino)-2-R-(2-benzthiazalylmethyl)succinyl]-S-phenylalanamide

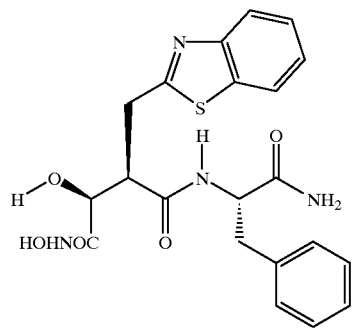

m.p. 165–167° C. 1H NMR, (d6 DMSO) 2.88 (1H, dd, J=14,8 Hz), 3.01–3.22 (4H, m), 4.06 (1H, app t, J=6.5 Hz), 4.28 (1H, dd, J=8,3 Hz), 5.80 (1H, d, J=6 Hz), 7.05–7.15 (6H, m), 7.38–7.51 (3H, m), 7.89 (1H, d, J=8 Hz), 8.02 (1H, d, J=7 Hz), 8.08 (1H, d, J=8 Hz), 8.95 (1H, s), 10.71 (1H, s).

Example 27

N'-[3S-Hydroxy-4-(N-hydroxyamino)-2R-{2-(4-nitrobenzyl)}succinyl]-S-phenylalanine-N-methylamide

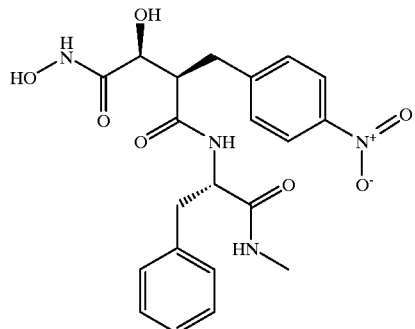

MH$^+$=445.

Example 28

N'-[3S-Hydroxy-4-(N-hydroxyamino)-2R-{2-(4-aminobenzyl)}succinyl]-S-5 phenylalanine-N-methylamide

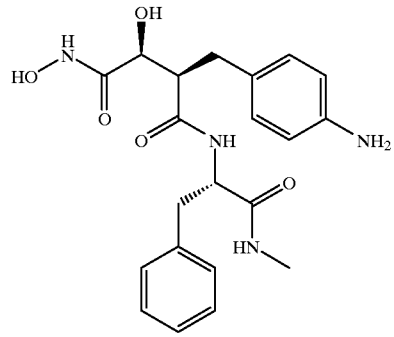

M$^+$=414.

Example 29

N'-[3S-Hydroxy-4-(N-hydroxyamino)-2R-{2-(4-benzoylaminobenzyl)}succinyl]-S-phenylalanine-N-methylamide

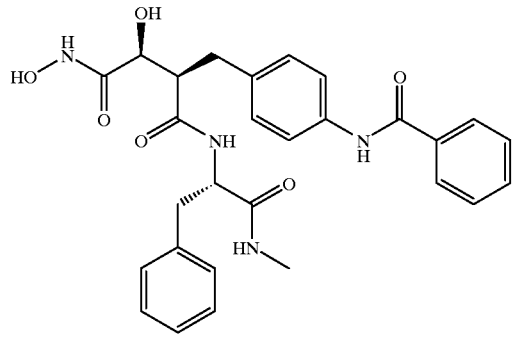

MNa$^+$=541.

Example 30

N'-[3S-Hydroxy-4-(N-hydroxyamino)-2R-{2RS-(1,2,3,4-tetrahydronaphthylmethyl)}succinyl]-S-phenylalanine-N-methylamide

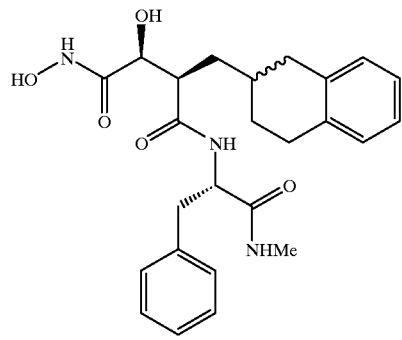

MNa⁺=476; ¹H NMR (d₆ DMSO) 1.07–1.45 (2H, m), 1.49–1.67 (2H, m), 2.10–2.31 (1H, m), 2.46 (3H, d, J=4.4 Hz, collapes to a singlet with D₂O), 2.51–2.65 (4H, m), 2.81–2.87 (2H, m), 3.06 (1H, d,d, J=4.2 & 8.0 Hz), 3.89 (1H, t, J=7.3Hz, collapes to a doublet, J=7.0 Hz with D2O), 4.30–4.47 (1H, m), 5.65 (1/3H, d, J=7.2 Hz, exchanges with D2O), 5.72 (2/3H, d, J=7.2 Hz, exchanges with D2O), 7.03–7.18 (9H, m), 7.80 (2/3H, q, J=4.3 Hz, exchanges with D2O), (7.89 (1/3H, q, J=4.3 Hz, exchanges with D2O), (7.98 (1H, d, J=8.25 Hz, exchanges with D2O), 8.88 (1H, s, exchanges with D2O), 10.66 (1H, s, exchanges with D2O).

Example 31

N'-[3S-Hydroxy-4-(N-Hydroxyamino)-2-R-(2-naphthylmethyl)succinyl]-S-tert-leucinamide

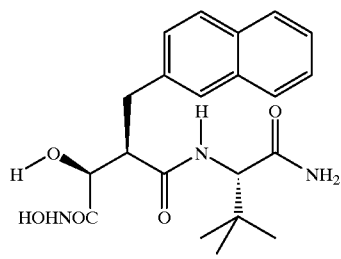

MNa⁺=424; ¹H NMR (d₆ DMSO) 0.90 (9H, s), 2.75 (1H, dd, J=13,5 Hz), 2.97–3.31 (2H, m), 3.84 (1H, t, JJ=7 Hz), 4.15 (1H, d, J=10 Hz), 5.61 (1H, d, J=8 Hz), 6.88 (1H, s), 7.242 (1H, s), 7.32 (1H, d, J=8 Hz), 7.45 (2H, m), 7.55 (1H, d, J=10 Hz), 7.63 (1H, m), 7.82 (3H, m), 8.88 (1H, s), 10.68 (1H, s).

Example 32

N'-[3S-Hydroxy-4-(N-Hydroxyamino)-2-R-(5-Benzothiophenylmethyl)succinyl]-S-phenylalanine-N-methylamide

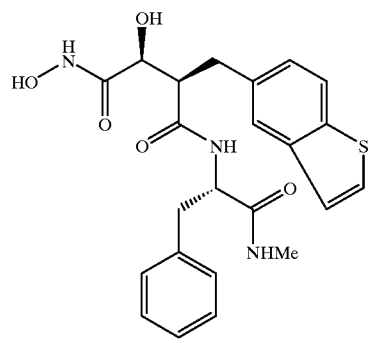

MH⁺=456, MNa⁺=478; ¹H NMR (d₆ DMSO) 2.36 (3H, d, J=4 Hz), 2.81–3.15 (5H, m), 3.92 (1H, m), 4.30 (1H, m), 5.78 (1H, d, J=6 Hz), 7.05 (1H, d, J=8 Hz); 7.17 (5H, m), 7.35 (2H, d, J=5.5 Hz), 7.52 (1H, s), 7.71 (1H, d, J=5 Hz), 7.83 (1H, d, J=8 Hz), 7.96 (1H, d, J=8 Hz), 8.92 (1H, s), 10.73 (1H, s).

Example 33

N'-[3S-Hydroxy-4-(N-hydroxyamino)-2R-(4-biphenylmethyl)succinyl]-S-phenylalanine-N-methylamide

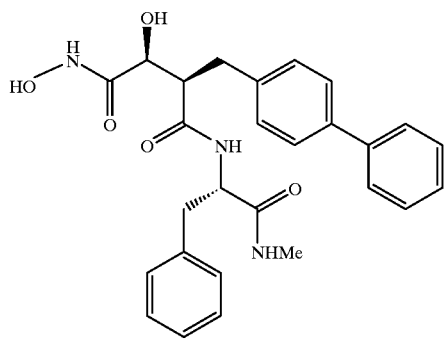

MH⁺=476, MNa⁺=498; ¹H NMR (d₆ DMSO) 2.44 (3H, d, J=5 Hz), 2.56–2.87 (4H, m), 3.01 (1H, dd, J=13.7, 5 Hz), 3.93 (1H, t, J=6.5 Hz), 4.31 (1H, m), 5.78 (1H, d, J=6 Hz), 7.10–7.65 (15H, m), 7.97 (1H, d, J=8 Hz), 8.92 (1H, s), 10.72 (1H, s).

Example 34

N'-[3S-Hydroxy4-(N-Hydroxyamino)-2-R-(2–5,6,7,8-tetrahydronaphthylmethyl) succinyl]-S-tert-leucine-N-methylamide

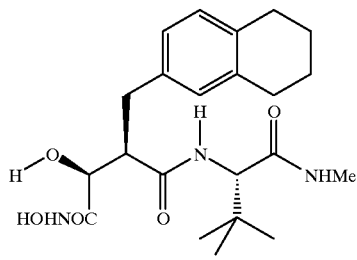

MNa⁺=442.

Example 35

N'-[3S-Hydroxy-4-(N-Hydroxyamino)-2-R-(1-naphthylmethyl)succinyl]-S-tert-leucine-N-methylamide

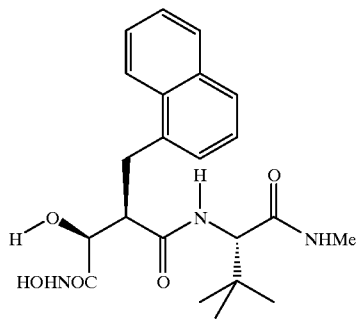

MNa+=438.

Example 36

N'-[3S-Hydroxy-4-(N-hydroxyamino)-2R-(4-benzyl)benzylsuccinyl]-S-phenylalanine-N-methylamide

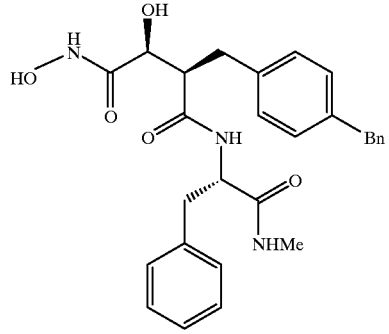

MNa⁺=512.

Example 37

N'-[3S-Hydroxy4-(N-hydroxyamino)-2R-(2-(3-quinolinyl)methyl)succinyl-S-phenyl-alaninamide.

¹H NMR (d₆ DMSO; 400 MHz) 2.83–3.02 (5H, m), 3.97 (1H, br. d), 4.28 (1H, m), 5.81 (1H, br. s), 6.98 (1H, br. s), 7.16 (5H, m), 7.28 (1H, br. m), 7.57 (1H, ddd, J=8, 7, 1 Hz), 7.70 (1H, ddd, J=8, 7, 1 Hz), 7.86 (1H, dd, J=8, 1 Hz), 7.95–7.99 (3H, m), 8.66 (1H, d, J=2 Hz), 8.91 (1H, br. s), 10.72 (1H, m).

Example 38

N'-[3S-Hydroxy-4-(N-hydroxyamino)-2R-(2-(3-quinolinyl)methyl)succinyl-S-tyrosinamide.

¹H NMR (d₆ DMSO; 400 MHz) 2.73–2.94 (5H, m), 3.97 (1H, br. t), 4.21 (1H, m), 5.84 (1H, br. d, J=6 Hz), 6.60 (2H, d, J=8 Hz), 6.95 (1H, br. s), 6.96 (2H, d, J=8 Hz), 7.24 (1H, br. s), 7.56 (1H, ddd, J=1 Hz), 7.69 (1H, ddd, J=8, 7, 1 Hz), 7.85–7.98 (4H, m), 8.66 (1H, d, J=2 Hz), 8.91 (1H, br. s), 9.13 (1H, s), 10.73 (1H, s).

Example 39

N'-[3S-Hydroxy-4-(N-hydroxyamino)-2R-(2-(6,7-difluoronaphthyl)methyl)succinyl-S-tyrosinamide.

¹H NMR (d₆ DMSO; 400 MHz) 2.67–2.87 (5H, m), 3.89 (1H, t, J=6 Hz), 4.16 (1H, m), 5.74 (1H, d, J=6 Hz), 6.56 (2H, d, J=8 Hz), 6.90 (1H, br. s), 6.92 (2H, d, J=8 Hz), 7.04 (1H, br. s), 7.21 (1H, d, J=8 Hz), 7.51 (1H, s), 7.73–7.92 (4H, m), 8.86 (1H, s), 9.09 (1H, s), 10.66 (1H, s).

Example 40

N'-[3S-Hydroxy-4-(N-hydroxyamino)-2R-(2-(6-hydroxynaphthyl)methyl)succinyl-S-phenylalaninamide ¹H NMR (d₆ DMSO; 400 MHz) 2.69–2.88 (4H, m), 3.01 (1H, dd, J=14,4 Hz), 3.90 (1H, t, J=6 Hz), 4.26 (1H, m), 5.83 (1H, d, J=6 Hz), 7.02–7.25 (10 H, m), 7.40 (1H, s), 7.53 (1H, d, J=8 Hz), 7.62 (1H, d, J=9 Hz), 7.95 (1H, d, J=8 Hz), 8.93 (1H, s), 9.64 (1H, s), 10.72 (1H, s).

Example 41

N'-[3S-Hydroxy-4-(N-hydroxyamino)-2R-(2-(6-fluoronaphthyl)methyl)succinyl-S-phenylalaninamide mp 198–201° C.; ¹H NMR (d₆ DMSO; 400 MHz) 2.74–2.93 (4H, m), 3.01 (1H, dd, J=14, 5 Hz), 3.93 (1H, t, J=6 Hz), 4.27 (1H, m), 5.78 (1H, d, J=6 Hz), 6.98 (1H, br. s), 7.16 (6H, m), 7.26 (1H, d, J=8 Hz), 7.37 (1H, m), 7.59 (1H, s), 7.63 (1H, dd, J=12, 2 Hz), 7.76 (1H, d, J=9 Hz), 7.86 (1H, m), 7.93 (1H, J=8 Hz), 8.90 (1H, s), 10.69 (1H, s).

Example 42

N'-[3S-Hydroxy4-(N-hydroxyamino)-2R-(2-(7-fluoronaphthyl)methyl)succinyl-S-phenylalaninamide.

mp 197–8° C.; ¹H NMR (d₆ DMSO; 400 MHz) 2.76–2.93 (4H, m), 3.01 (1H, dd, J=14, 5 Hz), 3.93 (1H, t, J=6 Hz), 4.28 (1H, m), 5.77 (1H, d, J=7 Hz), 6.99 (1H, br. s), 7.17 (7H, m), 7.34 (1H, m), 7.55 (2H, m), 7.80 (1H, d, J=8 Hz), 7.92 (2H, m), 8.90 (1H, s), 10.69 (1H, s).

Example 43

N'-[3S-Hydroxy-4-(N-hydroxyamino)-2R-(2-(6-quinolinyl)methyl)succinyl-S-phenyl-alaninamide.

mp 215–20° C.; ¹H NMR (d₆ DMSO; 400 MHz) 2.80–2.96 (4H, m), 3.01 (1H, dd, J=14, 5 Hz), 3.95 (1H, t,

J=6 Hz), 4.28 (1H, m), 5.79 (1H, d, J=6 Hz), 6.99 (1H, br. s), 7.15 (5H, m), 7.23 (1H, br. s), 7.44–7.50 (2H, m), 7.60, (1H, s), 7.87 (1H, d, J=9 Hz), 7.95 (1H, d, J=8 Hz), 8.23 (1H, d, J=8 Hz), 8.83 (1H, dd J=4, 1 Hz), 8.91 (1H, s), 10.70 (1H, s).

Example 44

N'-[3S-Hydroxy-4-(N-hydroxyamino)-2R-(2-(6-benzyloxynaphthyl)methyl)succinyl-S-phenylalaninamide mp 201–4° C.; $^1$H NMR (d$_6$ DMSO; 400 MHz) 2.75 (1H, m), 2.83–2.91 (3H, m), 3.01 (1H, dd, J=14, 5 Hz), 3.95 (1H, t, J=6 Hz), 4.28 (1H, ddd, J~8, 8, 5 Hz), 5.21 (2H, s), 5.78, d, J=6 Hz), 6.99 (1H, br. s), 7.17 (8H, m), 7.35 (2H, m), 7.41 (2H, m), 7.50 (3H, m), 7.64 (1H, d, J=8.5 Hz), 7.72 (1H, d, J=9 Hz), 7.91 (1H, d, J=8 Hz), 8.88 (1H, s), 10.67 (1H, s).

Example 45

Preparation of N'-[3S-Hydroxy-4-(N-hydroxyamino)-2R-(2-naphthylmethyl)succinyl]-S-tyrosinylamide.

a) N'-[2R-(2,2-Dimethyl-4-oxo-1,3-dioxalan-5S-yl)-3-(2-naphthyl)propanoyl]-S-tyrosinylamide.

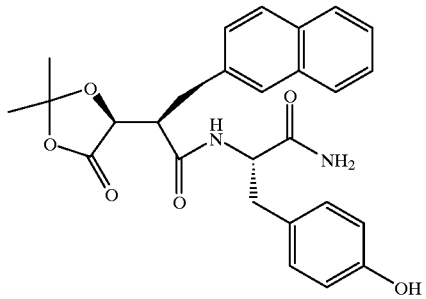

This compound was prepared by the general method described in Example 1(b) using S-tyrosinylamide in place of tert-leucine methylamide.

δH [(CD$_3$)$_2$SO] 1.47 (3H, s), 1.50 (3H, s), 2.69 (1H,ABq, J=13.8, 8.1 Hz), 2.82 (1H,ABq, J=13.8, 5.3 Hz), 3.14 (2H, m), 4.38 (1H, m), 4.49 (1H, d, J=6.2 Hz), 6.60 (2H, d, J=8.5 Hz), 6.96 (3H, m), 7.12 (1H, s), 7.38–7.55 (3H, m), 7.69 (1H, s), 7.79–8.00 (4H, m) and 9.16 (1H, s). MNa$^+$499 (+ve ion electrospray).

b) N'-[3S-Hydroxy-4-(N-hydroxyamino)-2R-(2-naphthylmethyl)succinyl]-S-tyrosinylamide.

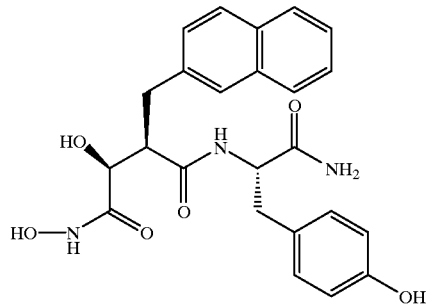

This compound was prepared by the general method described in Example 1 (c) using N'-[2R-(2,2-Dimethyl-4-oxo-1,3-dioxalan-5S-yl)-3-(2-naphthyl)propanoyl]-S-tyrosinylamide.

mp 179–180° C. δ$_H$[(CD$_3$)$_2$SO]2.70–3.00 (5H, m), 3.93 (1H, m), 4.20 (1H, m), 5.85 (1H, d, J=6.4 Hz), 6.60 (2H, d, J=8.2 Hz), 6.97 (3H, m), 7.23 (2H, s), 7.43–7.57 (3H, m), 7.72–7.92 (4H, m), 8.92 (1H, s), 9.17 (1H, s) and 10.72 (1H, s). (M–H)$^-$450 (–ve ion electrospray).

| | Activity Data | | |
|---|---|---|---|
| Compound | CD23 proteinase inhibition % | Collagenase inhibition IC50 uM | TNF processing inhibition % at 1 uM |
| Example 1 | 88 at 1 uM | >10 | — |
| Example 2 | 90 at 2 uM | 8.6 | 45 |
| Comparative Example* | 96 at 1 uM | 0.005 | 76.4 ± 0.9 |

*The comparative example was Example 2 of WO 90/05719, the compound of formula:

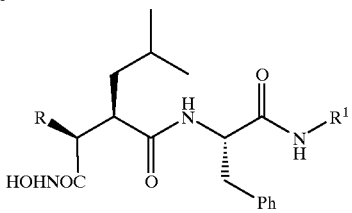

wherein R is CH$_2$S-(2-thienyl) and R$^1$ is methyl.

What is claimed is:
1. A compound of formula (I):

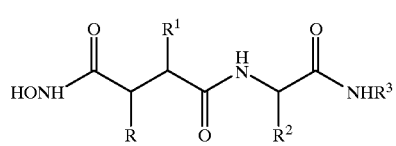

wherein:
R is hydroxy, hydrogen, alkyl, alkenyl, alkynyl or aryl;
R$^1$ is arylmethyl or heterocyclylmethyl;
R$^2$ is alkyl, alkenyl, aryl, cycloalkyl or cycloalkenyl; and
R$^3$ is hydrogen, alkyl, alkenyl, alkynyl or aryl;
with the proviso that;
if R$^1$ is phenylmethyl or naphthylmethyl, wherein the phenyl or naphthyl group is unsubstituted or substituted by up to five substituents selected from the group consisting of halogen, (C$_{1-6}$)alkyl, aryl(C$_{1-6}$)alkyl, (C$_{1-6}$)alkoxy, (C$_{1-6}$)alkoxy(C$_{1-6}$)alkyl, halo(C$_{1-6}$)alkyl, hydroxy, nitro, amino, mono- and di-N-(C$_{1-6}$)alkylamino, acylamino, acyloxy, carboxy, carboxy salts, carboxy esters, carbamoyl, mono- and di-N-(C$_{1-6}$)alkylcarbamoyl, (C$_{1-6}$)alkoxycarbonyl, aryloxycarbonyl, ureido, guanidino, sulphonylamino, aminosulphonyl, (C$_{1-6}$)alkylthio, (C$_{1-6}$)alkyl sulphinyl (C$_{1-6}$)alkylsulphonyl, heterocyclyl, heterocyclyl (C$_{1-6}$) alkyl, and a (C$_{3-5}$)alkylene chain linking two adjacent ring carbon atoms to form a carbocyclic ring; then R is hydroxy.
2. A compound according to claim 1, wherein R is hydroxy.
3. A compound according to claim 2, wherein R$^1$ is 1- or 2-naphthylmethyl.
4. A compound according to claim 2, wherein R is hydroxy, R$^1$ is optionally substituted benzyl; R$^2$ is t-butyl; and R$^3$ is hydrogen or methyl.

5. A compound according to claim 2, wherein
R is OH, $R^1$ is selected from the group consisting of 1-naphthylmethyl, 2-naphthylmethyl, 3-iodobenzyl, 4-methylbenzyl, 3-methylbenzyl, 2-methylbenzyl, benzyl, 2-phenylbenzyl, 4-azidobenzyl, 2-benzothiophenylmethyl, 2-benzofuranylmethyl, 7-methoxybenzofuranylmethyl, 2-(3-methyl)benzothiophenylmethyl, benzyloxybenzyl, 4-(prop-2-yl)benzyl, benzthiazalylmethyl, 2-(4-nitrobenzyl), 2-(4-aminobenzyl), 2-(4-benzoylaminobenzyl), 1,2,3,4-tetrahydronaphthylmethyl, 4-biphenylmethyl, 2-5,6,7,8-tetrahydronaphthylmethyl, (4-benzyl)benzyl, 2-(3-guinolinyl)methyl, 2-(6,7-difluoronaphthyl)methyl, 2,6-hydroxynaphthylmethyl, 6-fluoronaphthyl, 7-fluoronaphthyl, 2-(6-quinolinyl)methyl, 3,4-dimethylbenzyl and 2-(6-benzyloxynaphthyl), $R^2$ is t-butyl, benzyl or 4-hydroxybenzyl and $R^3$ is hydrogen or methyl.

6. A compound according to claim 2, selected from the group consisting of:

N'-[3S-Hydroxy-4-(N-hydroxyamino)-2R-(2-naphthylmethyl)succinyl]-S-tert-leucine-N-methylamide;

N'-[3S-Hydroxn-4-(N-hydroxyamino)-2R-(2-naphthylmethyl)succinyl]-S-phenylalanine-N-methylamide;

N'-[3S-Hydroxy-4-(N-hydroxyamino)-2R-(2-naphthylmethyl)succinyl]-S-phenylalaninamide;

N'-3S-Hydroxy-4-(N-hydroxyamino)-2R-(3-iodobenzyl)succinyl]-S-phenylalaninamide;

N'-[3S-Hydroxy-4-(N-hydroxyamino)-2R-(4-methylbenzyl)succinyl]-S-phenylalaninamide;

N'-[3S-Hydroxy-4-(N-hydroxyamino)-2R-(3-methylbenzyl)succinyl]-S-phenylalaninamide;

N'-[3S-Hydroxy-4-(N-hydroxyamino)-2R-(benzyl)succinyl]-S-phenylalaninamide;

N'-[3S-Hydroxy-4-(N-hydroxyamino)-2R-(2-methylbenzyl)succinyl]-S-phenylalanine N-methylamide;

N'-[3S-Hydroxy-4-(N-hydroxyamino)-2R-(benzyl)succinyl]-S-phenylalanine N-methylamide;

N'-[3S-Hydroxy-4-(N-hydroxyamino)-2R-(2-phenylbenzyl)succinyl]-S-phenylalanine N-methylamide;

N'-[3S-Hydroxy-4-(N-hydroxyamino)-2R-(3-iodobenzyl)succinyl]-S-tert-leucine N-methylamide;

N'-[3S-Hydroxy-4-(N-hydroxyamino)-2R-(4-methylbenzyl)succinyl]-S -tert-leucine N-methylamide;

N'-[3S-Hydroxy-4-(N-hydroxyamino)-2R-(3-methylbenzyl)succinyl]-S-tert-leucine N-methylamide;

N'-[3S-Hydroxy-4-(N-hydroxyamino)-2R-(benzyl)succinyl]-S-tert-leucine N-methylamide;

N'-[3S-Hydroxy-4-(N-hydroxyamino)-2R-(4-azidobenzyl)succinyl]-S-tert-leucine-N-methylamide;

N'-[3S-Hydroxy-4-(N-Hydroxyamino)-2-R-(2-Benzothiophenylmethyl)succinyl]-S-phenylalanamide;

N'-[3S-Hydroxy-4-(N-Hydroxyamino)-2-R-(3-Benzothiophenylmethyl)succinyl]-S-phenylalanine-N-methylamide;

N'-[3S-Hydroxy-4-(N-Hydroxyamino)-2-R-(2-Benzofuranylmethyl)succinyl]-S-phenylalanine-N-methylamide;

N'-[3S-Hydroxy-4-(N-Hydroxyamino)-2-R-(4-Hydroxybenzyl)succinyl]-S-phenylalanamide;

N'-[3S-Hydroxy-4-(N-Hydroxyamino)-2-R-(7-Methoxybenzofuranylmethyl)succinyl]-S-phenylalanine-N-methylamide;

N'-[3S-Hydroxy-4-(N-Hydroxyamino)-2-R-(2-(3-Methyl)benzothiophenylmethyl)succinyl]-S-phenylalanine-N-methylamide;

N'-[3S-Hydroxy-4-(N-Hydroxyamino)-2-R-(4-Benzyloxybenzyl)succinyl]-S-phenylalanamide;

N'-[3S-Hydroxy-4-(N-Hydroxyamino)-2-R-(3,4-Dimethylbenzyl)succinyl]-S-phenylalanine-N-methylamide;

N'-[3S-Hydroxy-4-(N-Hydroxyamino)-2-R-(4-(prop-2-yl)benzyl)succinyl]-S-phenylalanamide:

N'-[3S-Hydroxy-4-(N-hydroxyamino)-2R-(2-benzthiazalylmethyl)succinyl]-S-tert-leucine N-methylamide;

N'-[3S-Hydroxy-4-(N-Hydroxyamino)-2-R-(2-benzthiazalylmethyl)succinyl]-S-phenylalanamide;

N'-[3S-Hydroxy-4-(N-hydroxyamino)-2R-{2-(4-nitrobenzyl)}succinyl]-S-phenylalanine-N-methylamide;

N'-[3S-Hydroxy-4-(N-hydroxyamino)-2R-{2-(4-aminobenzyl)}succinyl]-S-phenylalanine-N-methylamide;

N'-[3S-Hydroxy-4-(N-hydroxyamino)-2R-{2-(4-benzoylaminobenzyl)}succinyl]-S-phenylalanine-N-methylamide;

N'-[3S-Hydroxy-4-(N-hydroxyamino)-2R-{2RS-(1,2,3,4-tetrahydronaphthylmethyl)}succinyl]-S-phenylalanine-N-methylamide;

N'-[3S-Hydroxy-4-(N-Hydroxyamino)-2-R-(2-naphthylmethyl)succinyl]-S-tert-leucinamide;

N'-[3S-Hydroxy-4-(N-Hydroxyamino)-2-R-(5-Benzothiophenylmethyl)succinyl]-S-phenylalanine-N-methylamide;

N'-[3S-Hydroxy-4-(N-hydroxyamino)-2-R-(4-biphenylmethyl)succinyl]-S-phenylalanine-N-methylamide;

N'-[3S-Hydroxy-4-(N-Hydroxyamino)-2-R-( 2-5 ,6,7,8-tetrahydronaphthylmethyl)succinyl]-S-tert-leucine-N-methylamide;

N'-[3S-Hydroxy-4-(N-Hydroxyamino)-2-R-(1-naphthylmethyl)succinyl]-S-tert-leucine-N-methylamide;

N'-[3S-Hydroxy-4-(N-hydroxyarnino)-2R-(4-benzyl)benzylsuccinyl]-S-phenylalanine-N-methylamide;

N'-[3S-Hydroxy-4-(N-hydroxyamino)-2R-(2-(3-quinolinyl)methyl)succinyl-S-phenyl-alaninamide;

N'-[3S-Hydroxy-4-(N-hydroxyamino)-2R-(2-(3-quinolinyl)methyl)succinyl-S-tyrosinamide;

N'-[3S-Hydroxy-4-(N-hydroxyamino)-2R-(2-(6,7-difluoronaphthyl)methyl)succinyl-S-tyrosinamide;

N'-[3S-Hydroxy-4-(N-hydroxyamino)-2R-(2-(6-hydroxynaphthyl)methyl)succinyl-S-phenylalaninamide;

N'-[3S-Hydroxy-4-(N-hydroxyamino)-2R-(2-(6-fluoronaphthyl)methyl)succinyl-S-phenylalaninamide;

N'-[3S-Hydroxy-4-(N-hydroxyamino)-2R-(2-(7-fluoronaphthyl)methyl)succinul-S-phenylalaninamide;

N'-[3S-Hydroxy-4-(N-hydroxyamino)-2R-(2-(6-guinolinyl)methyl)succinyl-S-phenyl-alaninamide;

N'-[3S-Hydroxy-4-(N-hydroxyamino)-2R-(2-(6-benzyloxynaphthyl)methyl)succinyl-S-phenylalaninamide; and N'-[3S-Hydroxy-4-(N-hydroxyamino)-2R-(2-naphthylmethyl)succinyl]-S-tyrosinylamide.

7. A compound according to claim 1, which is a compound of formula (IA):

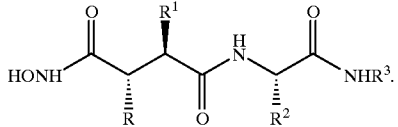

(IA)

8. A method for the treatment or prophylaxis of disorders in which the overproduction of s-CD23 is implicated, which method comprises the administration of a compound according to claim 1 to a human or non-human mammal in need thereof.

9. A pharmaceutical composition for the treatment or prophylaxis of disorders disorders in which the overproduction of s-CD23 is implicated which comprises a compound according to claim 1 and optionally a pharmaceutically acceptable carrier therefor.

10. A method for the treatment or prophylaxis of conditions mediated by TNF, which method comprises the administration of a compound according to claim 1 to a human or non-human mammal in need thereof.

11. A process for preparing a compound according to claim 1, which process comprises:

(a) deprotecting a compound of formula (II):

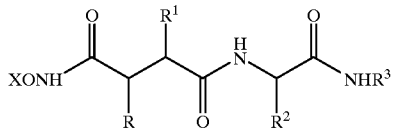

(II)

wherein R to $R^3$ are as defined in claims 1 to 8, and X is a protecting group, or (b) reacting a compound of formula (III):

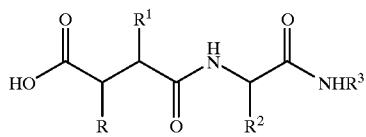

(III)

wherein R to $R^3$ are as defined in claim 1, and any hydroxy group is optionally protected, with hydroxylamine or a salt thereof, or (c) reacting a compound of formula (IV):

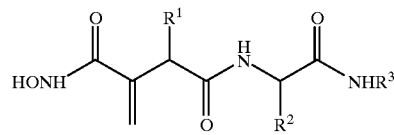

(IV)

wherein $R^1$ to $R^3$ are as defined in claim 1, with a thiol to give a compound of formula (I) wherein R is methyl substituted by alkylthio, arylthio, aralkylthio, or heterocyclylthio.

12. A compound of formula (II) as defined in claim 11 wherein R is hydroxy or protected hydroxy.

13. A compound of formula (IV) as defined in claim 11, wherein $R^1$ is heterocyclylmethyl.

14. A process for preparing a compound according to claim 2, which process comprises reacting a compound of formula (X):

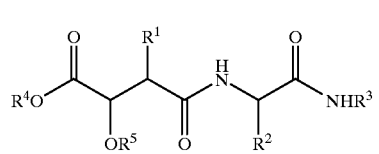

(X)

wherein $R^1$ to $R^3$ are as defined in claim 2, and $R^4$ and $R^5$ are the same or different and each is hydrogen or a hydroxy protecting group, or $R^4$ and $R^5$ together form a divalent hydroxy protecting group, with hydroxylamine or a salt thereof.

15. A compound according to claim 2 or 3 wherein $R^2$ is benzyl or t-butyl.

16. A compound according to claim 2 or 3 wherein $R^3$ is hydrogen or methyl.

17. A compound according to claim 15 wherein $R^3$ is hydrogen or methyl.

18. A method according to claim 8 wherein the disorder is allergy, an inflammatory disorder or autoimmune disease.

19. A pharmaceutical composition according to claim 9 wherein the disorder is allergy, an inflammatory disorder or autoimmune disease.

20. A process according to claim 11 wherein the protecting group is benzyl or trimethylsilyl.

* * * * *